United States Patent
Zobel

(10) Patent No.: US 9,829,697 B2
(45) Date of Patent: Nov. 28, 2017

(54) STEREO ENDOSCOPE SYSTEM

(71) Applicant: INTEGRATED MEDICAL SYSTEMS INTERNATIONAL, INC., Birmingham, AL (US)

(72) Inventor: Jurgen Zobel, Pembroke Pines, FL (US)

(73) Assignee: Integrated Medical Systems International, Inc., Birmingham, AL (US)

( * ) Notice: Subject to any disclaimer, the term of this patent is extended or adjusted under 35 U.S.C. 154(b) by 131 days.

(21) Appl. No.: 14/414,632

(22) PCT Filed: Jul. 15, 2013

(86) PCT No.: PCT/US2013/050525
§ 371 (c)(1),
(2) Date: Jan. 13, 2015

(87) PCT Pub. No.: WO2014/012103
PCT Pub. Date: Jan. 16, 2014

(65) Prior Publication Data
US 2015/0168710 A1 Jun. 18, 2015

Related U.S. Application Data

(60) Provisional application No. 61/671,345, filed on Jul. 13, 2012.

(51) Int. Cl.
*H04N 13/00* (2006.01)
*A61B 1/00* (2006.01)
(Continued)

(52) U.S. Cl.
CPC ........ *G02B 23/2415* (2013.01); *A61B 1/0019* (2013.01); *A61B 1/00105* (2013.01);
(Continued)

(58) Field of Classification Search
CPC . G02B 23/2415; H04N 13/0207; A61B 1/042
See application file for complete search history.

(56) References Cited

U.S. PATENT DOCUMENTS 4,235,506 A * 11/1980 Saito ...................... G02B 27/64
356/149
5,689,365 A * 11/1997 Takahashi .......... A61B 1/00179
348/E13.014
5,751,341 A * 5/1998 Chaleki .............. A61B 1/00045
348/45

(Continued)

*Primary Examiner* — Tsion B Owens
(74) *Attorney, Agent, or Firm* — C. Brandon Browning; Maynard, Cooper & Gale, PC

(57) ABSTRACT

Disclosed is a stereo endoscope system comprising stereo endoscopes of varying working lengths, working diameters and directions of view. Each stereo endoscope comprises two identical optical systems where every pair of corresponding components is permanently couple in a sideways orientation. The system is capable of withstanding harsh conditions associated with medical equipment cleaning and sterilization, particularly, the high temperatures and pressures associated with autoclaving. Each of the corresponding components of the two identical optical systems is paired and moved relative to each other to adjust focus and then affixed to create a new singular optical component. The system includes a prism block that extends the distance between the optical axes on the stereo endoscope to the position of two video chips.

18 Claims, 5 Drawing Sheets

(51) Int. Cl.
*G02B 23/24* (2006.01)
*A61B 1/04* (2006.01)
*A61B 1/055* (2006.01)
*H04N 13/02* (2006.01)
*H04N 5/225* (2006.01)

(52) U.S. Cl.
CPC .......... *A61B 1/00193* (2013.01); *A61B 1/042* (2013.01); *A61B 1/055* (2013.01); *H04N 5/2251* (2013.01); *H04N 13/0207* (2013.01); *H04N 13/0217* (2013.01); *H04N 2005/2255* (2013.01)

(56) References Cited

U.S. PATENT DOCUMENTS

| | | | | |
|---|---|---|---|---|
| 5,860,912 | A * | 1/1999 | Chiba | A61B 1/00059 348/45 |
| 8,556,807 | B2 * | 10/2013 | Scott | A61B 1/00193 600/166 |
| 8,734,328 | B2 * | 5/2014 | McDowall | G02B 5/04 600/109 |
| 9,192,286 | B2 * | 11/2015 | Kazakevich | A61B 1/0005 |
| 2009/0096865 | A1 * | 4/2009 | McKinley | G02B 23/2415 348/45 |
| 2009/0209940 | A1 * | 8/2009 | Nimkar | A61M 25/001 604/523 |
| 2012/0002956 | A1 * | 1/2012 | McDowall | A61B 1/00188 396/17 |
| 2014/0177043 | A1 * | 6/2014 | Togino | A61B 1/00193 359/367 |

* cited by examiner

STEREO ENDOSCOPE SYSTEM

FIELD OF THE INVENTION

The present invention is directed to a rigid endoscope system, and more particularly, to a stereo endoscope system.

BACKGROUND OF THE INVENTION

Medical endoscopes are used to inspect the interiors of human cavities. Such instruments include rigid endoscopes containing a lens system, flexible endoscopes containing a flexible image guiding bundle and video endoscopes.

In general, endoscopes are constructed with a diameter of only a few millimeters but are often several hundreds of millimeters long. Rigid endoscopes include an inner tube containing an optical system which relays an image of the cavity from the distal tip of the endoscope back to the proximal end of the endoscope. These endoscopes further contain an outer tube separated from the inner tube by a space filled with illumination fibers. The fibers guide externally created light into the internal cavity. The image relayed through the inner tube is observed at the proximal end by the operator. Additionally, a video camera may be utilized to capture the image.

Conventional rigid endoscopes possess a single optical viewing channel which provides a two-dimensional image of the viewing area. Endoscopes with a single optical system may, in some instances, create three-dimensional information about an object. For instance, objects at different distances may appear differently sized, while overlapping of objects indicate which object is in front and which is in the back. For many surgical endoscopic procedures this three dimensional information is sufficient and stereoscopic vision is unnecessary. However, more complex surgical procedures require a more specific reproduction of the viewing area, including a better view of the spatial relationships between objects. Many of these procedures utilize robotic assistance requiring stereo endoscopic observation for instrument control.

Stereoscopic systems in general produce two images which display an object from slightly different perspectives, i.e., a left and right image. The human brain is able to merge these two slightly different images, received from the left and right eyes, and create a three-dimensional impression. For example, DE 164944 (1904) discloses an instrument with two separate optical viewing paths which permits viewing an object from two different directions from a position opposite the distal end of the endoscope. The proximal part of the endoscope is connected to a double eyepiece which simultaneously permits viewing of the object with both eyes. DE 209083 describes an endoscope accessory which separates the exit pupil of a monoscopic visual instrument into left and right parts with slightly different perspectives. These two basic constructions are still used in most conventional stereo endoscope systems.

It is often advantageous to use a two optical endoscopic system with a larger eye base, particularly in surgical procedures involving the abdomen. Although a two optical path system provides better stereoscopic visualization, technical problems may also arise. Endoscopic optical systems may expand and contract during exposure to heat during the sterilization process. In addition, the lens system may move, resulting in shifting of the focus and magnification of the two images. Slight exposure to mechanical shock or movement can cause instrument misalignment.

What is needed in the art, therefore, is a cost effective stereo endoscope system with a larger eye base that avoids misalignment during use and sterilization. The camera utilized with the instrument should adapt to fit endoscopes with varying diameters and directions of view.

SUMMARY OF THE INVENTION

The present disclosure embodies a stereo endoscope system comprising stereo endoscopes of varying working lengths, working diameters and directions of view. Each stereo endoscope comprises two identical optical systems where every pair of corresponding components is permanently couple in a sideways orientation. The system is capable of withstanding harsh conditions associated with medical equipment cleaning and sterilization, particularly, the high temperatures and pressures associated with autoclaving. Each of the corresponding components of the two identical optical systems is paired and moved relative to each other to adjust focus and then affixed to create a new singular optical component.

In one embodiment, the present invention pertains to a stereo endoscope system comprising a plurality of stereo endoscopes with differing working lengths, working diameters and directions of view, where each of the plurality of stereo endoscopes comprises two identical optical systems where every pair of corresponding components is permanently couple in a sideways orientation, and a stereo video camera removeably coupled to any of the plurality of stereo endoscopes in two 180-degree reversed positions. In additional embodiment, the stereo video camera comprises a flat prism block positioned between the stereo endoscope and the optical element of the stereo video camera. The prism block may further comprise two coupled prisms and may extend the optical axes of the two identical optical systems. In a further embodiment, the corresponding optical components of each of the plurality of endoscopes are paired, optically aligned and affixed.

In one example, the oculars of each of the plurality of endoscopes comprise a diameter equal to the diameter of the relay lenses, and the oculars of each of the plurality of endoscopes are rod lenses. In some instances, the rod lenses are aligned along the optical axes of the two identical optical systems. In one embodiment, the paired identical optical systems are aligned inside a common tube and the inner diameter of the tube embraces the out shape of the paired identical optical systems. The common tube may then be inserted into an outer tube.

In an additional embodiment, the stereo video camera further comprises a first and a second objective aligned along each of the optical axes of the two identical optical systems. The stereo video camera may also further comprise a first video chip aligned in the focus of the first objective and a second video chip aligned in the focus of the second objective. In one embodiment, the objectives of the stereo video camera are mechanically connected and move along a common axis parallel to the optical axes of the stereo video camera. In an additional embodiment, the objective lenses of the first objective are moveable independently of the objective lenses of the second objective.

In an additional example, each of the pairs of corresponding optical components further comprise a flat ground surface and the components may be permanently affixed at the location of each of the ground surfaces. In one example, each of the two rod lenses forming the ocular is separated into two segments by an air gap.

DETAILED DESCRIPTION

The present invention is directed to a system comprising stereo endoscopes of varying working lengths, working diameters and directions of view. Each stereo endoscope comprises two identical optical systems where every pair of corresponding components is permanently couple in a sideways orientation. Every pair of corresponding components in the optical systems is permanently couple using permanent means. The system further comprises a stereo video camera removeably coupled to any of the plurality of stereo endoscopes in two 180-degree reversed positions. The system is capable of withstanding harsh conditions associated with medical equipment cleaning and sterilization, particularly, the high temperatures and pressures associated with autoclaving.

Figure 1A:
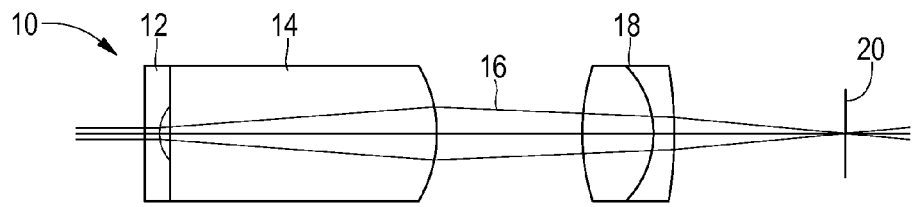
FIG. 1A is a side view of a conventional monoscopic endoscope.
Figure 1B:
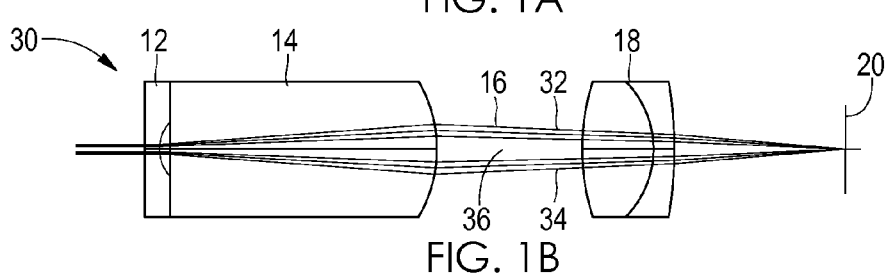
FIG. 1B is a side view of a monoscopic endoscope which has been converted to a stereo endoscope.

FIGS. 1A, 1B 2A and 2B illustrate the tip of a conventional endoscope including the objective. FIG. 1A illustrates a conventional monoscopic endoscope 10. Monoscopic endoscope 10 includes a negative lens 12, an objective lens 14, a light bundle 16, a field lens 18 and a first intermediate image 20. Turning now to FIG. 1B, an endoscope is illustrated with the light bundle 14 separated into a small left 32 and right 34 portion by blocking the center portion 26 of light bundle 16. In this manner, the monoscopic endoscope 10 functions as a stereo endoscope 30 comprising a single optical system.

Figure 2A:
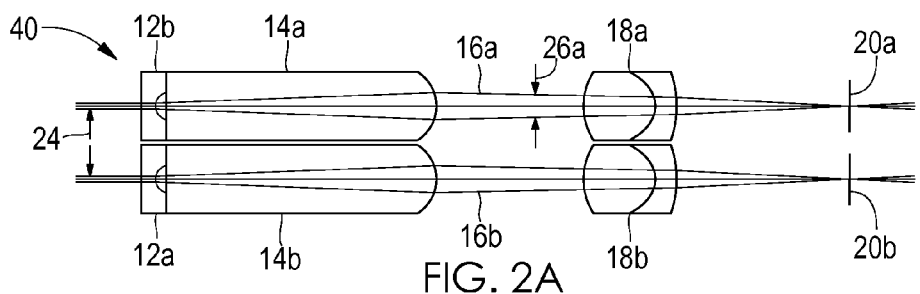
FIG. 2A is a side view of an embodiment of a stereo endoscope with two optical systems.
Figure 2B:
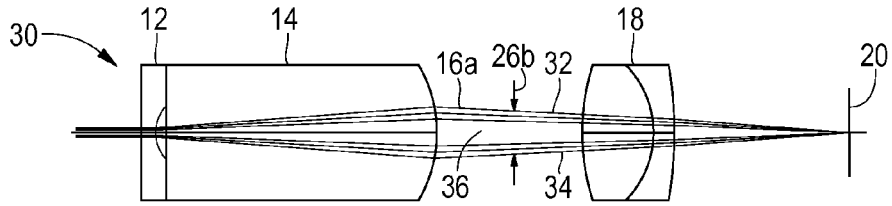
FIG. 2B is a side view of a monoscopic endoscope which has been converted to a stereo endoscope.

FIGS. 2A and 2B illustrate the structural differences between a stereo endoscope with two optical systems and an endoscope with one optical system. FIG. 2B illustrates a stereo endoscope 30 as described above with reference to FIG. 1B. Here a single monoscopic optical system is transformed to a stereo endoscope by separating light bundle 16 into a small left 32 and right 34 portions. This is accomplished through blocking the center portion 36 of light bundle 14. FIG. 2A illustrates a stereo endoscope 30 with two optical systems 22a and 22b. Each optical system 22a and 22b is comprised of identically sized components (i.e., negative lenses 12a and 12b, object lenses 14a and 14b, light bundles 16a and 16b and field lenses 18a and 18b). Two images 20a and 20b are produced. The two optical systems 22a and 22b are positioned in a side-by-side orientation. However, the components of the two systems 22a and 22b are not affixed and, as a result, may move relative to the one another. This may cause the stereo endoscope 30 to become misaligned. The dual system 40 illustrates in FIG. 2A has the advantage of having a greater eye base 24 (i.e., the distance between the optical axes of the two optical systems 22a and 22b) and a greater entrance pupil 26a and 26b (i.e., the diameter of the light bundle 16). A smaller eye base 28 provides for poorer depth perception, particularly in instances where the endoscope is not immediately adjacent to the structure to be viewed.

Figure 9:
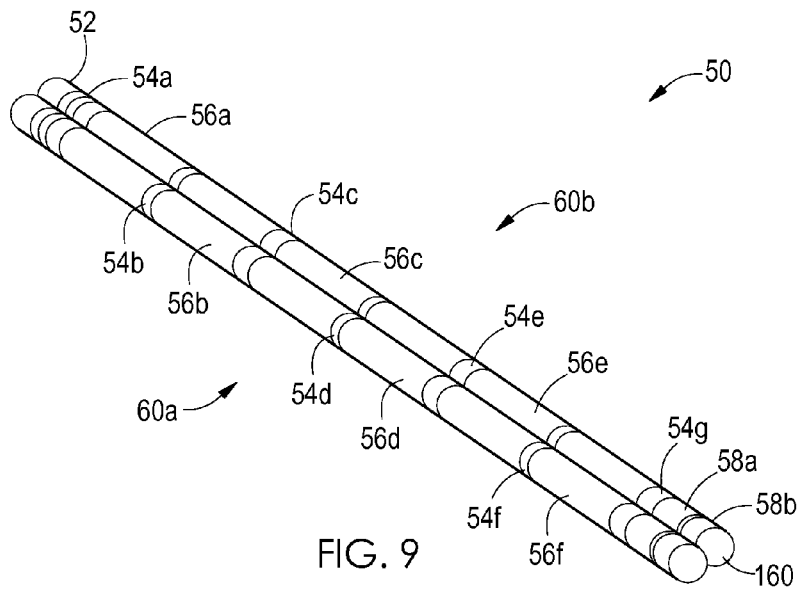
FIG. 9 is a perspective view of an embodiment of a stereo endoscope of the invention comprising two identical optical systems with paired corresponding optical components.

The multi-optical stereo endoscope of the system of the present disclosure is produced from conventional optical components. These components, for example objective lenses and relay lenses, are fixed on a tool along the circular periphery of the lenses. Referring to FIG. 9, there is depicted an embodiment of the stereo video system of the present invention comprising two optical systems with identically paired corresponding optical components. Here, two identical optical systems 60a and 60b are aligned in a parallel orientation. Each optical system 60a and 60b comprises a series of identical components, for instance two object lens objectives 52a and 52b, a series of paired rod lenses 56a-f and two sets of oculars 58a and 58b. These components are divided by a series of sets of air gaps 54a-g and collectively comprise optical relay system 62. One of skill in the art will recognize that the relay system 62 may be of any size as required for a particular application. As an example, the relay system could include only two sets paired rod lenses 56a and 56b, or it may include a series of ten paired rod lenses 56. In addition, the optical systems 60a and 60b may be of any diameter needed for the intended application.

Figure 10:
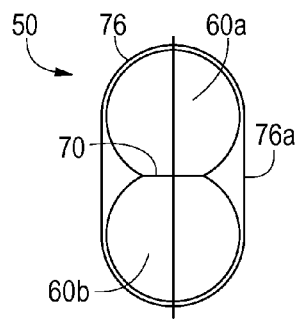
FIG. 10 is a cross sectional view of an embodiment of two identical optical components of the invention comprising ground surfaces encased in tubing.
Figure 11:
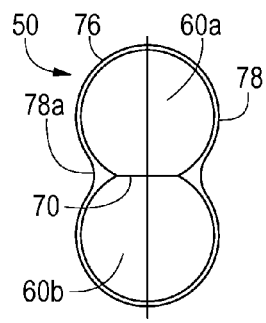
FIG. 11 is a cross sectional view of an additional embodiment of two identical optical systems of the invention comprising ground surfaces and encased in formed tubing.
Figure 12:
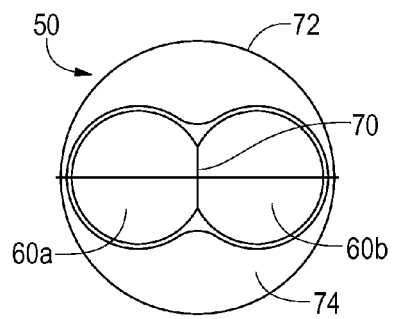
FIG. 12 is a cross sectional view of an embodiment of two identical optical systems of the invention comprising ground surfaces, encased in tubing and inserted into outside tubing.

Referring now to FIGS. 10-12, which illustrate a cross section of optical component 60a and 60b, the optical components 60a and 60b may include a ground surface 70 which extends along the length of the component 60a or 60b. This surface 70 is ground onto the optical components, for instance the object lens objectives 52, the paired rod lenses 56 and oculars 58, which allows the pairs of components to fit or align against each other in a sideways alignment. Each component 60a and 60b is then paired, optically aligned and permanently joined. The components 60a and 60b are joined by methods known to one of skill in the art, for example by application of an adhesive. Other methods of permanently joining the components are possible without deviation from the currently disclosed invention. Once permanently joined, the two components 60a and 60b may move together as a single component, but they may not move independently relative to each other. As a result, components 60a and 60b never change their common focus.

Turning again to FIG. 10, the permanently adhered components 60a and 60b are affixed at their ground surfaces 70. This surface 70 provides a flat bonding area and a greater surface area for adherence. The components are encased in rigid tubing 76 which provides a flat outer surface 76a. In the embodiment illustrated in FIG. 11, the flat outer tubing 78 includes a recessed area 78a which provides a figure-eight appearance. The inner diameter of the tubing 78 embraces the outer shape of the components 60a and 60b. FIG. 12 illustrates an embodiment of encased optical components 60a and 60b from FIG. 10 after insertion into outer tube 72. The stereo endoscope 50 may rotate within outer tube 72 to provide additional fields of view within the body cavity.

In an additional embodiment not illustrated in the figures, optical components 60a and 60b retain their rounded surfaces (i.e., no grinding of the outer surface). In this example (not shown), the optical components 60a and 60b are permanently joined along their cylindrical surfaces. The lack of a flat bonding area provides a smaller surface area for joining the components 60a and 60b, resulting in a weaker bond. The bonding of the rounded surfaces may be strengthened by further processing the adhesive, for instance by blackening. This embodiment may be an appropriate candidate for use with the figure-eight shaped tubing described in FIG. 11, which may provide additional support and stability to optical components 60a and 60b.

Figure 3:
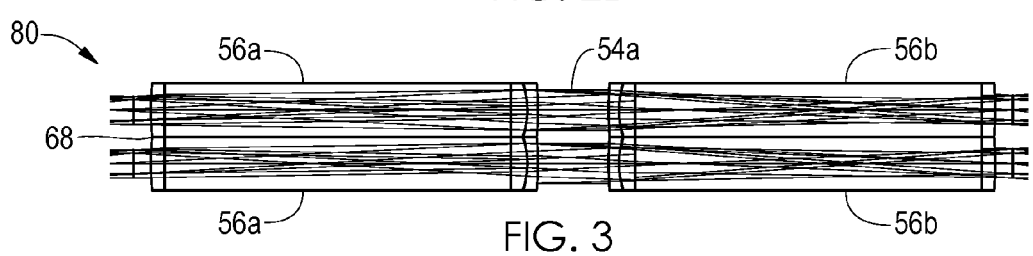
FIG. 3 is a side view of two identical rod lenses joined at cylindrical surfaces in an embodiment of a stereo endoscope system of the invention.
Figure 4:
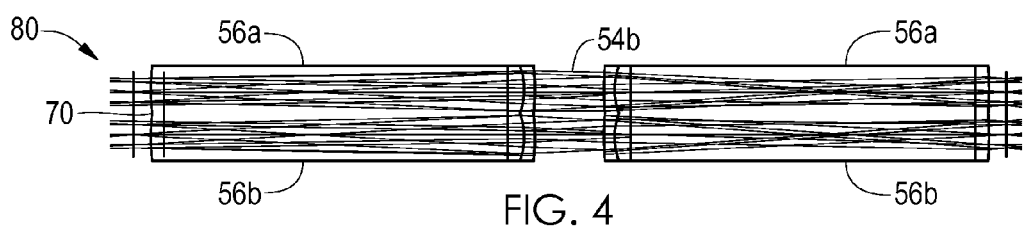
FIG. 4 is a side view of two identical rod lenses joined at flat surfaces in an embodiment of a stereo endoscope system of the invention.

FIGS. 3 and 4 illustrate the difference between ground and unground (i.e., curved) joined surfaces with optical components. FIG. 3 demonstrates a relay system 80 comprising two identical pairs of rod lenses 56a and 56b with an intervening air gap 54. Here, the rod lenses contain no ground or flat surfaces but rather comprise curved surfaces, as illustrated by line 68. As described above, the curved or cylindrical surface 68 provide a smaller surface area for joining the rod lenses 56a and 56b, resulting in a weaker bond. In contrast, FIG. 4 illustrates a relay system 80 including flat surfaces 70. The two lens pairs 56a and 56b are permanently adhered at flat surface 70 which provides a flat bonding area and a greater surface area for adherence.

By way of example, a stereo endoscope with a total diameter of 10 mm typically includes a lens diameter of approximately 4.5 mm. A ground side of 0.1 mm results in a flat bonding surface with a side length of 1.33 mm. Such a surface provides an adequate bonding area with an adjacent component. An endoscope with these dimensions provides an eye base of approximately 4.3 mm. A rounded endoscope (i.e., containing no ground surfaces) provides bonding along a glue gap of 0.02 mm. In the present example above with, a lens diameter of 4.5 mm will result in a bonding surface with a side length of only 0.2 mm.

The presently disclosed stereo endoscope provides the advantages of a large eye base in a single system. Specifically, the permanently joined components may expand or contract together as a whole during autoclaving or other sterilization procedures, but the individual optical components will not move relative to one another. The distance between the optical axes of the two optical components does not change, while the prism system (discussed below) will not shift during sterilization or usage.

Figure 5:
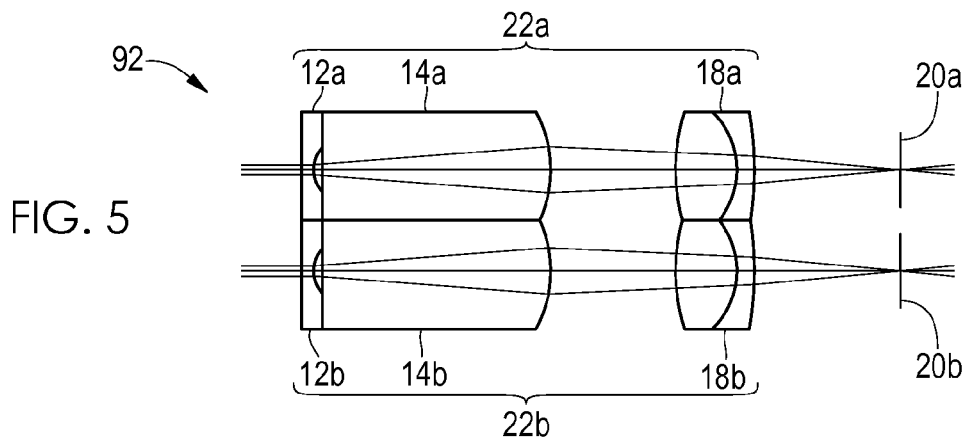
FIG. 5 is a side view of an embodiment of a stereo endoscope system of the invention with paired objective and field lenses.

FIG. 5 illustrates an objective system 80 of the present invention. Here, identical pairs of negatives 12a and 12b, objective lenses 14a and 14b, and field lenses 18a and 18b have been paired, optically aligned and then permanently joined. In contrast to the non-adhered system 40 illustrated in FIG. 2A, the permanently joined optical component pairs of systems 22a and 22b (i.e., objective lenses 14a and 14b and filed lenses 18a and 18b) may move together as a single component, but they may not move independently relative to each other. As a result, components 14a, 14b, 18a and 18b never change their common focus and now function as a single stereo endoscope 92.

The filed lenses 18a and 18b may be paired in the same way as the relay lenses (i.e., rod lenses 56a-g discussed in reference to FIG. 9). Objective lenses 14a and 14b with attached circular deflection prisms (not shown) have similar flat surfaces but these lenses must be manufactured as left and right components. The negatives 12a and 12b are normally positioned in front of a prism (not shown in FIG. 5) which must possess a smaller diameter when compare to other optical components. As a result, the negatives 12a and 12b are generally aligned with the circular deflection prisms (not shown) and adhered after alignment of the objective lenses 14a and 14b. As discussed above, the filed lenses 18a and 18b and objective lenses 14a and 14b may be adhered absent the presence of a flat ground surface. This results in a much weaker bond.

Monoscopic endoscopes generally include oculars with a larger diameter as compared to the remaining optical components. These large oculars are positioned in the housing at the proximal end of the endoscope, i.e., placed outside of the body cavity, and provide a larger area for the physician to manipulate. The large oculars with an attached prism combination required with stereo endoscopes are very expensive, particularly because the components must be capable of withstanding normal sterilization procedures like autoclaving. In order to solve this problem, the presently disclosed stereo endoscope does not include a prism block positioned within the endoscope. Instead, the objective of the optical system serves the function of the prism block.

However, the ocular then cannot have a diameter bigger than that of the rod lenses and the objective lenses.

Figure 6:
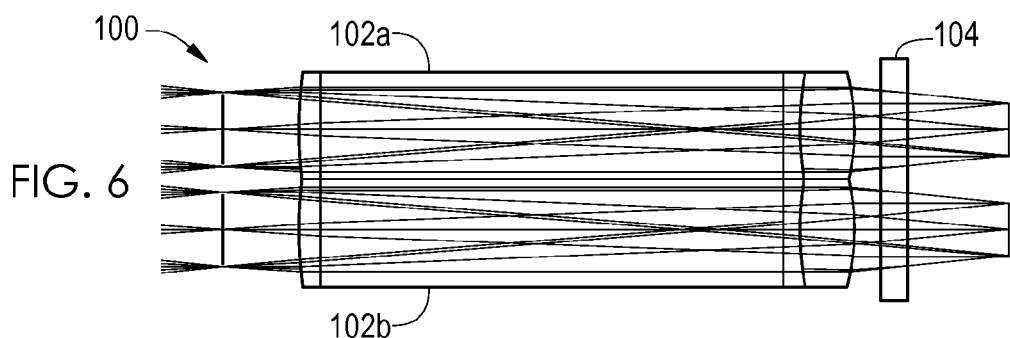
FIG. 6 is a side view of an ocular comprising a single short rod lens pair in an embodiment of a stereo endoscope system of the invention.

FIG. 6 illustrates an ocular 100 comprising a single rod lens pair 102a and 102b which act as left and right ocular lenses. The rod lenses 102a and 102b are similar to the rod lenses illustrated in FIGS. 3 and 4, but they are shorter in length and the ocular 100 does not include an air gap or any additional rod lens pairs. The rod lenses 102a and 102b have an outer diameter equal to the diameter of the relay and objective lenses (not shown). Rod lenses 102a and 102b are aligned and adhered using methods described above for other optical materials. The ocular 100 further includes a common window 104 which seals the internal components of the stereo endoscope from the outside atmosphere.

Figure 7:
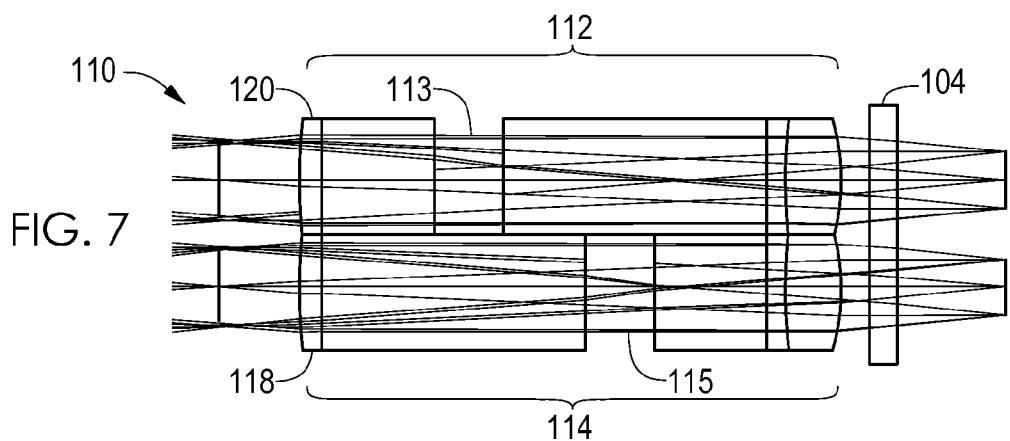
FIG. 7 is a side view of an ocular comprising a single short rod lens pair and offset air gaps in an embodiment of a stereo endoscope system of the invention.
Figure 8:
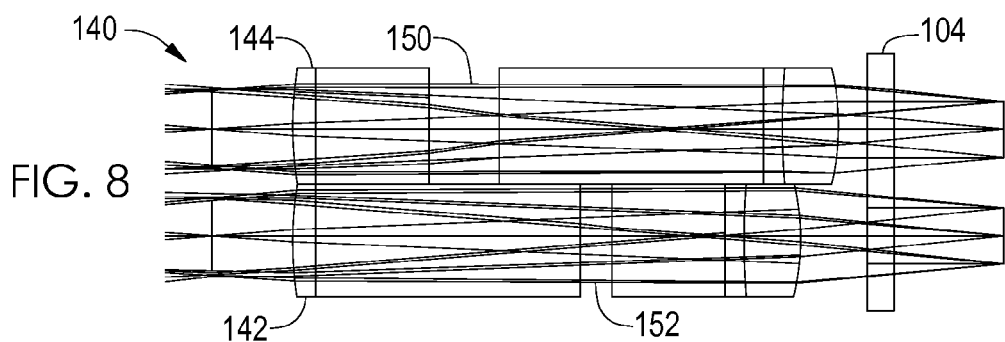
FIG. 8 is a side view of an ocular comprising a single short rod lens pair and differently sized air gaps in an embodiment of a stereo endoscope system of the invention.

The ocular 100 illustrated and described in reference to FIG. 6 has a higher magnification as compared to the relay rods. This higher magnification is adjusted by introducing air gaps in the rod lenses. FIG. 7 illustrates an ocular lens with a left ocular 114 and a right ocular 116. The left ocular 118 includes rod lens 114 with an intervening air gap 115, while the right ocular 120 includes a rod lens 112 with an intervening air gap 113. As illustrated in FIG. 7, air gapes 113 and 115 are introduced at different positions along the length of rod lenses 112 and 114. Turning now to FIG. 8, ocular lens 140 includes a left ocular 142 comprising a rod lens 152 and an intervening air gap. Right ocular 144 includes a right rod lens 148 and an air gap 150 that is sized smaller than air gap 152. Placing the left and right air gaps at different locations, or including left and right air gaps of different sizes, allows for the slight adjustment of the focal lengths. This provides equal magnifications and focal positions. As with the optical systems described above, the left and right rod lenses are aligned and adhered to prevent movement relative to each other. These components may be sterilized, for instance by autoclaving, while still maintaining a constant focus and magnification.

Figure 13:
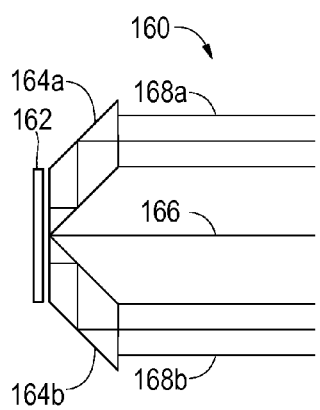
FIG. 13 is a top view of an embodiment of a prism block of the video camera of the presently disclosed stereo endoscope system.
Figure 14:
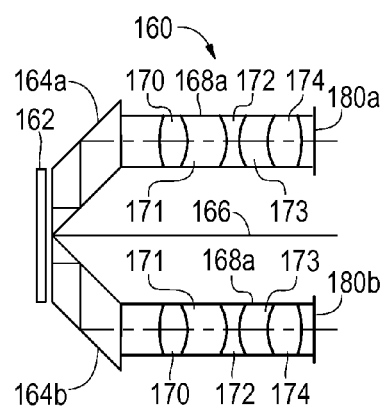
FIG. 14 is a top view of an embodiment of a prism block and objectives of the video camera of the presently disclosed stereo endoscope system.

The stereo endoscope components utilized in the present invention are closely spaced. As a result, it is very difficult to position a large prism block within the confines of the stereo endoscope. The stereo endoscope system of the present invention therefore provides a stereo video camera prism block which is separate from the endoscopes. The stereo video camera may be coupled to endoscopes of varying lengths and diameters. FIG. 13 illustrates an exemplary stereo video camera prism block 160 of the invention. The prism block 160 is positioned between the stereo endoscope and the optical elements of the video camera (see FIG. 9) at the site of the endoscope/video camera connection. The prism block 160 functions to extend the two optical axes of the stereo endoscope a distance that is equal to the distance between two video chips (discussed in detail below). A window 162 defines the point of demarcation between the stereo endoscope described above and the stereo video endoscope of the present system. Two prisms 164a and 164b extend the optical axis 166 of the light bundle to the left 168a and right 168b sides, thus ensuring that the two exit pupils of the stereo endoscope are separate. The prisms 164a and 164b also ensure that the two video chips (not shown in FIG. 13) may be positioned in the prism block 160 in close proximity to each other. Turning now to FIG. 14, the prism block 160 further includes a series of camera objective lenses. These objective lenses are positioned within the optical path of each prism 164a and 164b in the following order: a first b-convex lens 170, followed by an air gap 171, a b-concave lens 172, a second air gap 173 and a second b-convex lens 174. A third air gap 175 is positioned between the second b-convex lens 174 video chips 180a and 180b. These objectives form an image on the pair of video chips 180a and 180b. The distance between the optical axes 168a and 168b is equal to the distance between video chips 180a and 180b. The distance between the optical axes 168a and 168b is created such that it is equal to the eye base 24 (see FIG. 2A) of the largest endoscope included in the stereo endoscope system.

The presently disclosed stereo endoscope system includes a video chip with the capability of transmitting and recording images. The video chips required for complex surgical procedures are generally larger that the distance between the two optical axes 24 (as described in reference to FIG. 2A). By way of example, the distance between the optical axes of two optical systems is roughly 1 mm to 5 mm as calculated from the outer diameter of the stereo endoscope. A set of video chips with a diameter of approximately 12 mm requires a separation of at least 13 mm to 14 mm.

Figure 15:
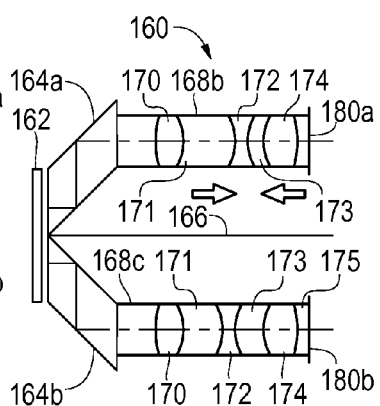
FIG. 15 is a top view of an embodiment of a prism block and the focal length alignment of a group of optical components of the video camera of the presently disclosed stereo endoscope system.

As illustrated in FIG. 15, the focal length of the objectives 170, 172 and 174 illustrated at the top of the figures may be adjusted to match the focal length of the objectives 170, 172 and 174 illustrated in the bottom of the figure. Each of the top objectives 170, 172 and 174 may be moved independently along the optical axis 168b to adjust the focus length, as indicated by the two arrows. The entrance pupils (not shown) of the pairs of objectives are located within the prism block 160. The size of the entrance pupils (not shown) is limited only by the size of prisms 164a and 164b.

Figure 16:
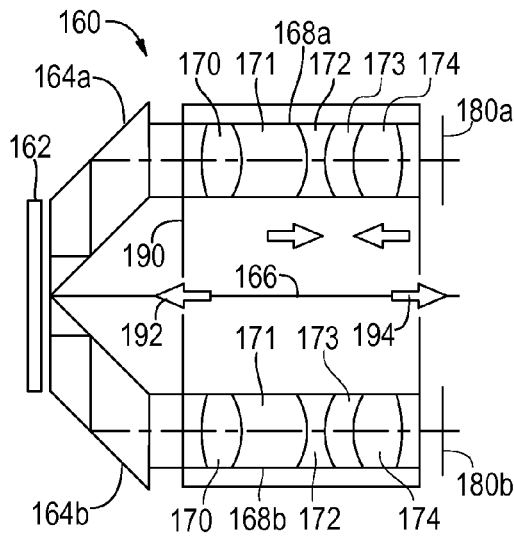
FIG. 16 is a top view of an embodiment of a prism block and the focus adjustment of the objectives of the video camera of the presently disclosed stereo endoscope system.
Figure 17:
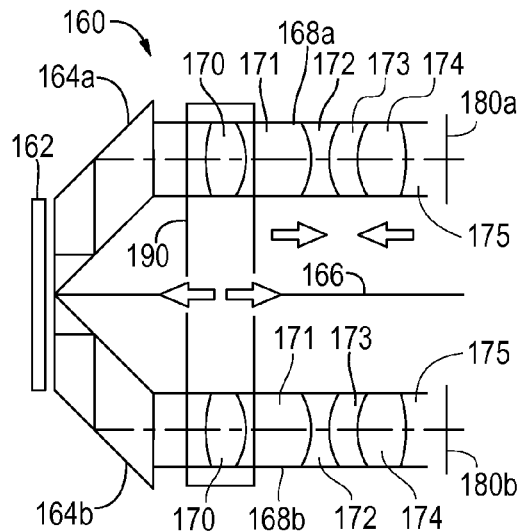
FIG. 17 is a top view of an additional embodiment of the focus adjustment of the objectives of the video camera of the presently disclosed stereo endoscope system.

In contrast to the optical components of the stereo endoscope described in detail previously, the video camera lenses 170, 172 and 174 cannot be permanently adhered because the distance between each lens is too great. As a result, the focus of these lenses may become misaligned due to small movements. As described above, it is often disadvantageous to locate the video camera focus adjustment components in the stereo endoscope as it may interfere with its operation. The stereo video endoscope of the present invention instead locates the focus adjustment functions in the video camera. To overcome the problems discussed previously, lenses 170, 172 and 173 may be adhered to a common block. FIG. 16 illustrates an embodiment where each lens 170, 172 and 173 is adhered to one common block or board 190 after adjusting the focal length as described in reference to FIG. 15. All of the optical components 170, 172 and 174 of both objectives are mechanically connected and moved along a common axis parallel to the two optical axes of the stereo video camera. Both sets of objective lenses may be moved in a forward or backwards direction, as indicated by arrows 192 and 194, to adjust the focus. In an additional embodiment exemplified in FIG. 17, only one of the three lens pairs, in this example lens 170, is adhered to a common board 190. These lenses 170 are moved together along a common axis in either the forward 194 or backwards direction 192 to adjust the focus of the stereo video camera.

Figure 18:
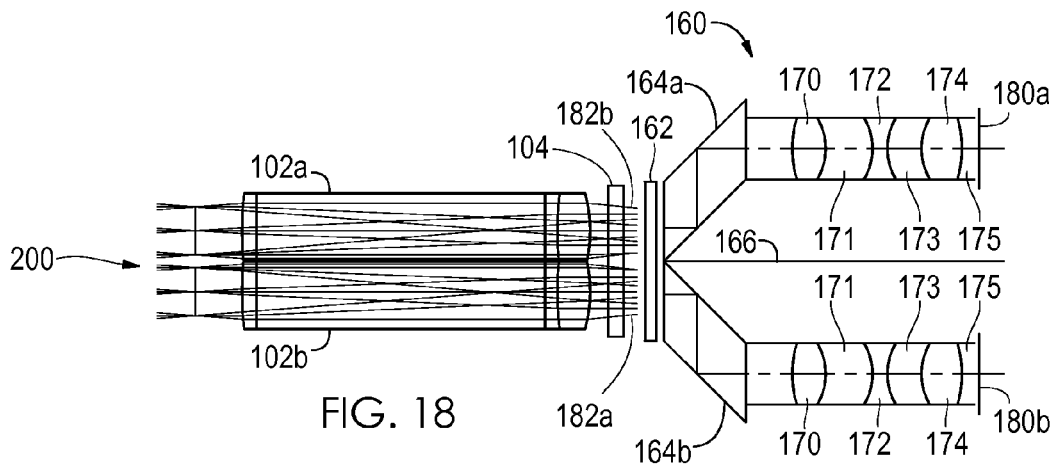
FIG. 18 is a top view of an embodiment of a stereo endoscope system of the invention with differing pupil diameters.
Figure 19:
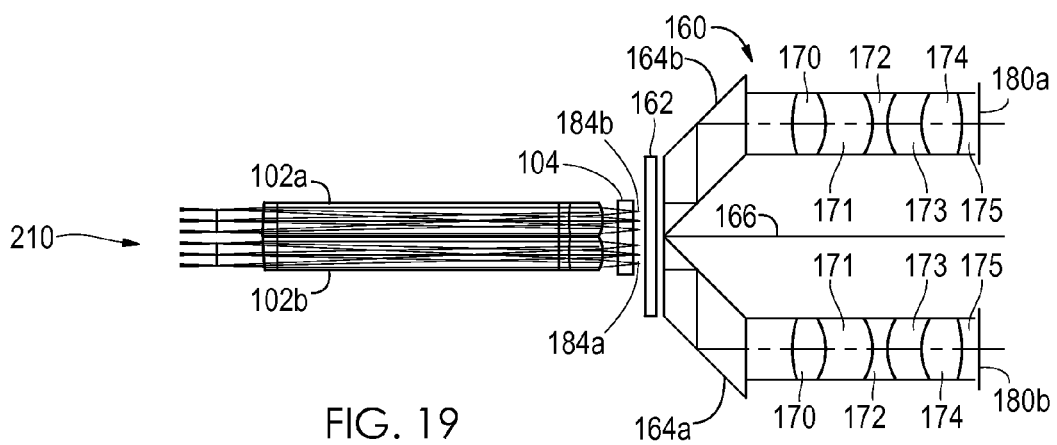
FIG. 19 is a top view of an additional embodiment of a stereo endoscope system of the invention with differing pupil diameters.
Figure 20:
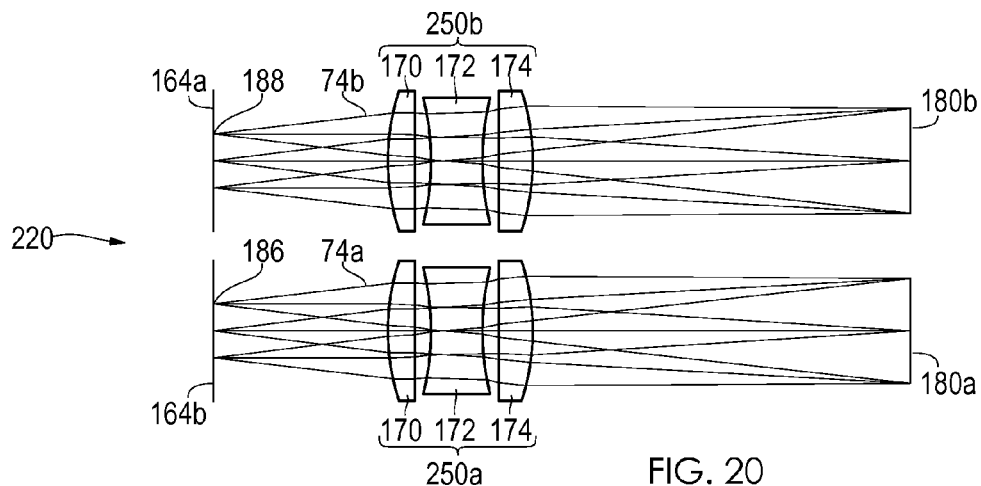
FIG. 20 is a top view of an embodiment of a stereo endoscope system of the invention with a maximum pupil diameter.
Figure 21:
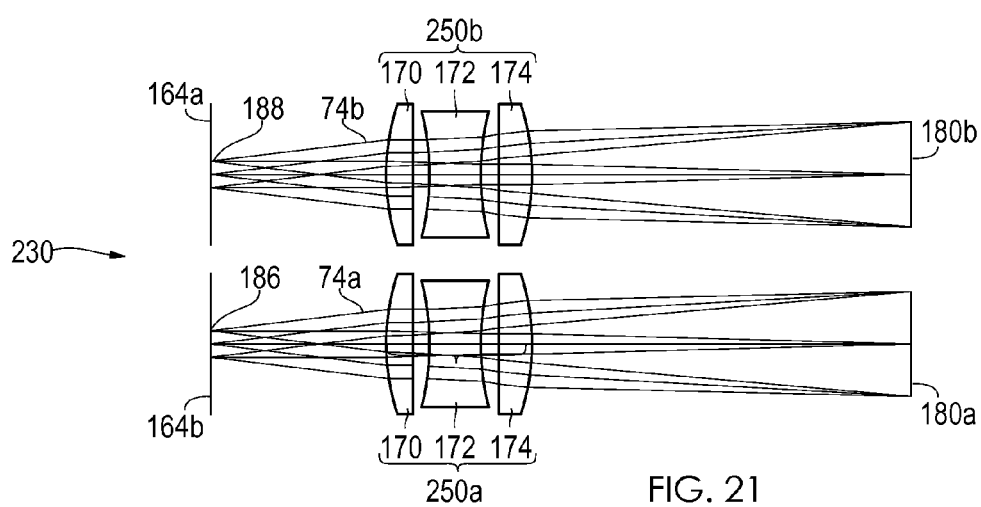
FIG. 21 is a top view of an embodiment of a stereo endoscope system of the invention with exit pupils sized smaller than entrance pupils.
Figure 22:
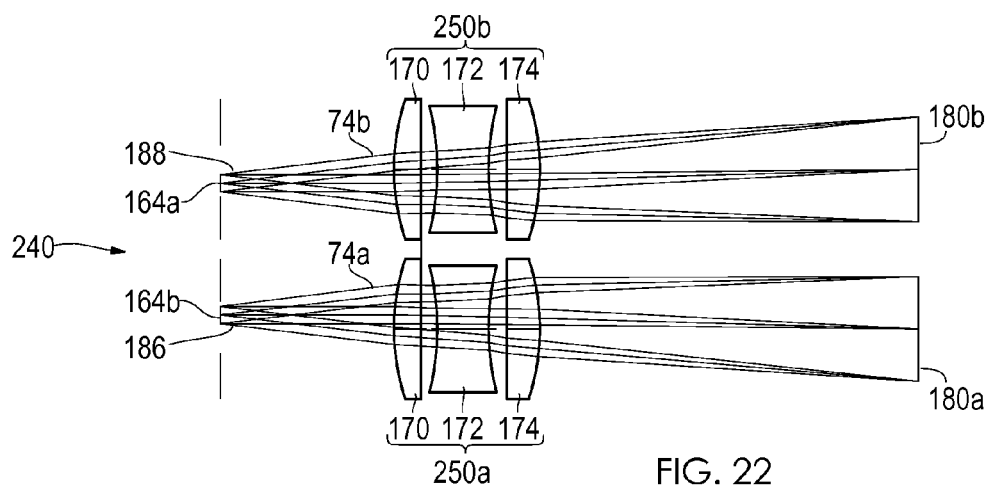
FIG. 22 is a top view of an additional embodiment of a stereo endoscope system of the invention where the exit pupils are off axis.

The exit pupils of any of the differently sized stereo endoscopes utilized in the presently described stereo endoscope system will fit within the entrance pupils of the corresponding objectives in the common stereo video camera. Stereo endoscopes with different lens diameters and differently sized optical axes may be connected to one common video camera. FIG. 18 illustrates a stereo endoscope 200 with large lenses 102a and 102b, large exit pupils 182a and 182b and a large window 104. In contrast, the stereo endoscope 210 of FIG. 19 includes smaller lenses 102a and 102b, smaller exit pupils 184a and 184b and a smaller window 104. The same stereo video camera and prism block 160 may be connected to each endoscope. The illumination bundles 74a from the left optical system are fully captured by the left prism objectives 170, 172 and 174 while the illumination bundles 74b from the right optical system are fully captured by the right prism objectives 170, 172 and 174. The entrance pupils (not shown) of the left and right objectives 170, 172 and 174 are large enough so that all the illumination bundles 74a and 74b pass through the objectives even if they enter the objectives in an off-axis configuration. FIGS. 20-22 represent the video camera objectives 170, 172 and 174 as illustrated in FIGS. 13-19. The prisms 164a and 164b are not included in FIGS. 20-22 in order to simplify the following discussion. FIG. 20 illustrates large entrance pupils 186 and 188 emanating from a larger stereo endoscope 220. The illumination bundles 74a and 74b are centered in front of objectives 170, 172 and 174. Referring to FIG. 21, the entrance pupils 186 and 188 are sized smaller than the entrance pupils of the objectives 170, 172 and 174 and thus produce smaller illumination bundles 74a and 74b. These smaller light bundles 74a and 74b pass through a smaller portion of the entrance pupils (not shown) of the video camera objectives 170, 172 and 174. FIG. 22 illustrates an endoscope 240 with smaller entrance pupils 186 and 188 which enter the left 250a and right 250b objectives at a slightly off-axis orientation relative to the optical axes of the objectives 170, 172 and 174. This asymmetry occurs as a result in the difference in the distance between the entrance pupils observed with the differently sized endoscopes. FIGS. 18-22 illustrate that neither the size of the entrance pupil nor the entrance point on the objective lenses affects the function of the stereo video camera and prism block as presently described. As such, a single stereo video camera may be utilized in the present invention with multiple endoscopes of various lengths and diameters. The single stereo video camera may be coupled to a first endoscope, utilized in a particular process or procedure, uncoupled from the first stereo endoscope, coupled to a second stereo endoscope, etc.

The alignment of the optics in the stereo endoscopes relative to the stereo video camera must be securely maintained by mechanical means. The stereo endoscopes must be retained in a fixed position at the point of attachment with the stereo video camera by various means as are known to one of skill in the art. In one embodiment, the stereo endoscopes are secured with a bayonet type mechanical adapter. Stereo endoscopes with a deflective mechanism must fit the adapter in two 180 degree opposed positions.

It is claimed:

1. A stereo endoscope system comprising:
   a plurality of stereo endoscopes with differing working lengths, working diameters and directions of view, wherein each of the plurality of stereo endoscopes comprises two identical optical systems where every pair of corresponding components is permanently coupled in a sideways orientation; and
   a stereo video camera removeably coupled in succession to any of the plurality of stereo endoscopes in two 180-degree reversed positions,
   wherein each of the pairs of corresponding optical components further comprise a flat ground surface and each of the pairs of corresponding optical components are permanently affixed at the location of each of the flat ground surfaces.

2. The stereo endoscope system of claim 1, wherein the stereo video camera comprises a flat prism block positioned between the stereo endoscope and the optical element of the stereo video camera.

3. The stereo endoscope system of claim 2, wherein the prism block further comprises two coupled prisms.

4. The stereo endoscope system of claim 3, wherein the prism block extends the optical axes of the two identical optical systems.

5. The stereo endoscope system of claim 1, wherein the corresponding optical components of each of the plurality of endoscopes are paired, optically aligned and affixed.

6. The stereo endoscope system of claim 1, wherein the oculars of each of the plurality of endoscopes comprise a diameter equal to the diameter of the relay lenses.

7. The stereo endoscope system of claim 6, wherein the oculars of each of the plurality of endoscopes are rod lenses.

8. The stereo endoscope system of claim 7, wherein the rod lenses are aligned along the optical axes of the two identical optical systems.

9. The stereo endoscope system of claim 1, wherein the paired identical optical systems are aligned inside a common tube.

10. The stereo endoscope system of claim 9, wherein the inner diameter of the tube embraces the out shape of the paired identical optical systems.

11. The stereo endoscope system of claim 9, wherein the common tube is inserted into an outer tube.

12. The stereo endoscope system of claim 4, wherein the stereo video camera further comprises a first and a second objective aligned along each of the optical axes of the two identical optical systems.

13. The stereo endoscope system of claim 12, wherein the stereo video camera further comprises a first video chip aligned in the focus of the first objective and a second video chip aligned in the focus of the second objective.

14. The stereo endoscope system of claim 12, wherein the objectives of the stereo video camera are mechanically connected and move along a common axis parallel to the optical axes of the stereo video camera.

15. The stereo endoscope system of claim 12, wherein the objective lenses of the first objective are moveable independently of the objective lenses of the second objective.

16. The stereo endoscope system of claim 7, wherein each of the two rod lenses forming the ocular are separated into two segments by an air gap.

17. A stereo endoscope system comprising:
   a first a endoscopic optical system including first objective lens assembly and a first relay lens assembly, the first objective lens assembly and the first relay lens assembly including first lenses, each of the first lenses having a first flat sidewall portion,
   a second endoscopic optical system including a second objective lens assembly and a second relay lens assembly, the second objective lens assembly and the second relay lens assembly including second lenses that correspond to the first lenses, each of the second lenses having a second flat sidewall portion, and
   a stereo video camera operatively coupled to the first endoscopic optical system and the second endoscopic optical system,
   wherein the first flat sidewall portion of each first lens is rigidly coupled to the second flat sidewall portion of each second lens corresponding thereto.

18. A stereo endoscope system comprising:
   a first a endoscopic optical system including first lenses, each of the first lenses having a first flat sidewall portion,
   a second endoscopic optical system including second lenses that correspond to the first lenses, each of the second lenses having a second flat sidewall portion, and a stereo video camera operatively coupled to the first endoscopic optical system and the second endoscopic optical system,
wherein the first flat sidewall portion of each first lens is coupled to the second flat sidewall portion of each second lens corresponding thereto.

* * * * *